US005650432A

United States Patent [19]
Walker et al.

[11] Patent Number: 5,650,432
[45] Date of Patent: Jul. 22, 1997

[54] METHOD OF TREATING OR PREVENTING NON-VIRAL MICROBIAL INFECTION

[75] Inventors: Edward B. Walker; Richard A. Mickelsen, Jr.; Jennifer N. Mickelsen, all of Ogden, Utah

[73] Assignee: JLB, Inc., Ogden, Utah

[21] Appl. No.: 409,703

[22] Filed: Mar. 24, 1995

[51] Int. Cl.$^6$ .......................... A61K 31/35; A61K 31/045; A61K 35/78
[52] U.S. Cl. ............................................. 514/456; 514/724
[58] Field of Search ...................... 514/456, 724, 514/54; 424/195.1

[56] References Cited

U.S. PATENT DOCUMENTS

| | | | |
|---|---|---|---|
| 3,963,700 | 6/1976 | Philip | 260/236.5 |
| 4,083,779 | 4/1978 | Combe et al. | 210/23 H |
| 4,309,207 | 1/1982 | Devlin | 71/79 |
| 4,652,448 | 3/1987 | Sadowski | 424/87 |
| 4,775,477 | 10/1988 | Stahl et al. | 210/641 |
| 4,857,327 | 8/1989 | Virdalm | 424/195.1 |
| 5,128,100 | 7/1992 | Hollis et al. | 422/14 |
| 5,200,186 | 4/1993 | Gabetta et al. | 424/195.1 |

FOREIGN PATENT DOCUMENTS

| | | |
|---|---|---|
| 1054899 | 10/1991 | China . |
| 3027933 | 2/1981 | Germany . |
| 3427014 | 1/1986 | Germany . |
| 9013304 | 11/1990 | WIPO . |
| 9206695 | 4/1992 | WIPO . |

OTHER PUBLICATIONS

Payless Drug Stores Coupon, "Cranberry Extract" advertisement (published before Mar. 24, 1995).
CRC Handbook of Fruit Set and Development, pp. 114, 115, 117.
I. Ofek, et al., "Anti-*Escherichia Coli* Adhesin Activity Of Cranberry And Blueberry Juices", vol. 324, No. 22, p. 1599.
Fuleki et al., "Quantitative Methods for Anthocyanins. 1. Extraction and Determination of Total Anthocyanin in Cranberries.", Journal of Food Science, vol. 33, pp. 72–76 (1968).
Fuleki et al., "Quantitative Methods for Anthocyanins. 3. Purification of Cranberry Anthocyanins", Journal of Food Science, vol. 33, pp. 266–274 (1968).
Marwan et al., "Microbial Inhibitors of Cranberries", Journal of Food Science, vol. 51, No. 4, pp. 1009–1013 (1986).
Official Methods of Analysis of the Association of Official Analytical Chemists, pp. 424–425 (1984).
Fuski et al., "Flavonol Glycosides in Cranberries", Journal of Food Science, vol. 32, pp. 527–530 (1967).
The Merck Index, An Encyclopedia of Chemicals, Drugs, And Biologicals, pp. 291, 452, 453, 640, 857, 941, 999 (1989).
Sephadex LH–60 chromatography in organic solvents, Pharmacia Fine Chemicals.
Sobota, "Inhibition Of Bacterial Adherence By Cranberry Juice: Potential Use For The Treatment Of Urinary Tract Infections", The Journal of Urology, vol. 131, May, pp. 1013–1016.
Sunset Western Garden Book, pp. 207, 208, 435, 436 (1988).
Wang et al., "Isolation And Characterization Of Polyphenolic Compounds In Cranberries", Journal of Food Science, vol. 43, No. 5, pp. 1402–1404 (1978).
Welsh et al., "Great Basin Naturalist Memoirs A Utah Flora", Brigham Young University, Provo, Utah, No. 9, p. 605 (1987).
Zafriri et al., "Inhibitory Activity of Cranberry Juice on Adherence of Type 1 and Type P Fimbriated Escherichia coil to Euracroytic Cells", Antimicrobial Agents and Chemotherapy, vol. 33, No. 1, pp. 92–98 (Jan. 1989).

*Primary Examiner*—John W. Rollins
*Attorney, Agent, or Firm*—Trask, Britt & Rossa

[57] ABSTRACT

Proanthocyanidin monomers, dimers, polymers, flavonoid, and flavanoid derivatives and related compounds are used for their ability to interfere with bacterial adherence to a surface. Crystalline proanthocyanadin dimer and plant extracts enriched with such compounds are also disclosed.

21 Claims, 7 Drawing Sheets

METHOD OF TREATING OR PREVENTING NON-VIRAL MICROBIAL INFECTION

TECHNICAL FIELD

The invention relates to various compounds having therapeutic and other uses, and more particularly to compounds which inhibit the adhesion of bacteria to a surface.

BACKGROUND

Flavonoid and proanthocyanidin polymers having a varying number of flavonoid units are known and have been reported, for example, in W. L. Mattice, et al., *Phytochemistry*, 23, p. 1309–1311 (1984); Z. Czochanska, et al., *J. C. S. Chem. Comm.*, 375 (1979); W. T. Jones, et al., *Photochemistry*, 15, p. 1407–1409 (1976); E. Haslam, *Plant Polyphenols*, p. 75 (1989). Compounds such as proanthocyanidin polymers have been previously described as having anti-viral activity. See, e.g. International Publication Number WO/92/06695 to Shaman Pharmaceuticals, Inc. and International Publication Number WO 90/13304 to Cariel et al. These compounds have been extracted from various plant materials such as Croton and Calophyllum plant species.

DISCLOSURE OF THE INVENTION

The invention includes the use of compounds having biological activity measurable as inhibition of adhesion of bacterial cells to surfaces, and a plant extract which is significantly enriched for this anti-adhesion activity. The specific compounds used include procyanidins, leucocyanin and leucodelphinin, and flavonol glucosides including myricetin-3-pyranoside. An exemplary, preferred procyanidin compound is a substituted epicatechin-catechin dimer.

These components have a structure selected from I, II, III, IV, and V, and their esters, or ethers or the corresponding oxonium salts

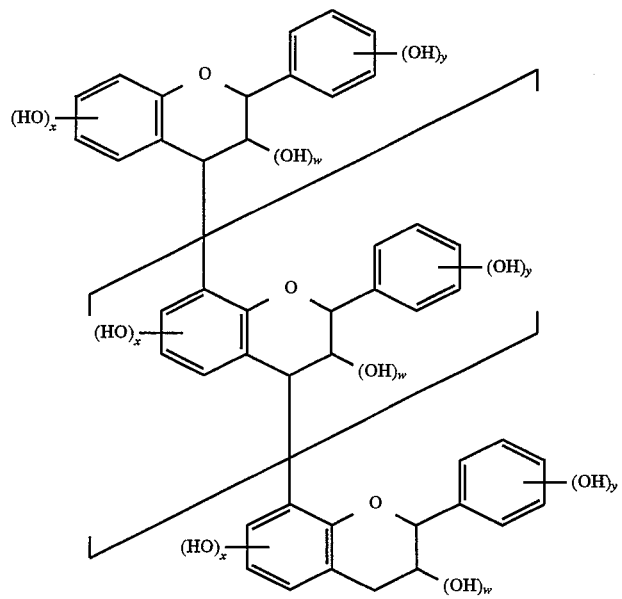

I

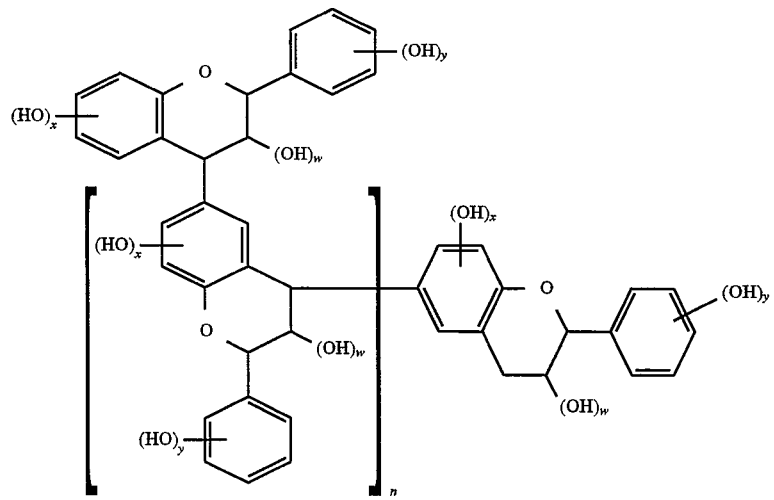

II

-continued

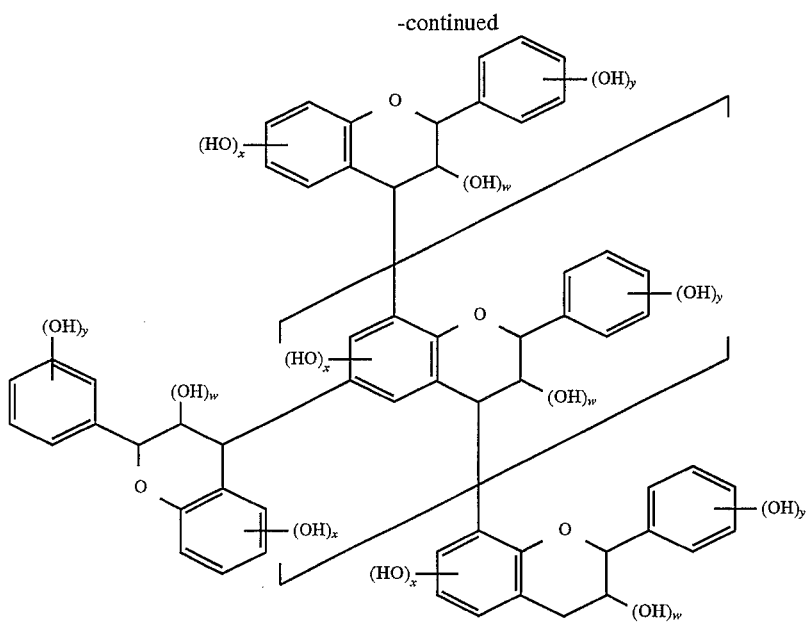

wherein x, y=0 to 3, w=0 or 1, n=0 to 16 for formula (I) or (II), and, in the case of formula (III), n=0 to 8 (preferably n=0 to 6 or 7 for formula (III).

The monomer comprises a composition of formula (IV) or formula (V):

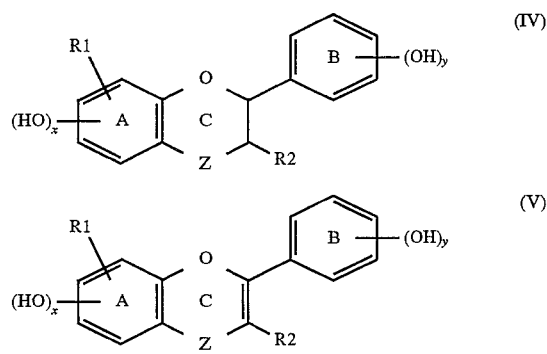

x=0–3; y=0–3; Z=CH$_2$, CHOH, C=O, CHSO$_3$H, galloyl, catechin, or epicatechin; R$^1$=H, pyranoside, galloyl, catechin, or epicatechin; and R$^2$=H, pyranoside, galloyl, or hydroxy.

The proanthocyanidin polymer useful for treating non-viral microbial infection can comprise 2 to 18 monomeric flavanoid units having structure (IV), or esters, ethers or corresponding oxonium salts thereof.

The invention also includes the use of metabolically-altered polyphenolic substances herein described such as catechin glucumnide and/or 3'-o-methyl-(+)-catechin glucuronide and/or 3'-o-methyl-(+)-catechin sulfate [82249-08-9], preserving the intact flavonol ring system. These metabolically activated substances and other chemically-activated glucuronides and/or sulfates of phenolic substances such as epicatechin, catechin, myrecitin, quercitin, quercitin, rutin, and the like.

Another aspect of the invention relates to a method of treating non-viral infections comprising administering, to a warm-blooded animal, a therapeutically effective mount of anti-adherence agent comprising a proanthocyanidin monomer polymer containing two to eighteen flavonoid units. The flavonoid units include but are not limited to catechins, epicatechins, gallocatechins, galloepicatechins, flavanols, flavonols, flavandiols, leucocyanidins, leucodelphinidin anthocyanidins, or combinations thereof. The flavonoid units can be singly or double linked to each other. The proanthocyanidin polymer can be administered intravenously, intraperitoneally, subcutaneously, intramuscularly, orally, topically, or by inhalation.

The present invention also relates to proanthocyanidins useful for treating non-viral infections in general having a structure selected from I through V, above, and esters, ethers and corresponding oxonium salts thereof, where n=zero to eighteen, preferably zero to thirteen, most preferably zero to nine.

The invention also includes a method of making the compounds by extracting them from plant material and then purifying them.

The invention also includes a method of inhibiting the adhesion of bacteria to both biological and non-biological surfaces using the compounds.

The anti-adhesion property of the extract is useful in a number of areas. For example, the cleaning of industrial fermentation equipment, medical and dental instruments, laboratory culture jars, and the like may be accomplished with the extract. The extract may further be useful in inhibiting the adhesion of bacteria to surgical implants, tooth surfaces, and oral cell types found in the mouth, and to cells in the urinary tract of humans and/or animals.

A method of inhibiting the adhesion of bacteria includes the steps of providing a compound and applying the compound in a suitable medium to a surface believed to have bacteria such as E. coli adhered thereto to disengage the bacteria from the surface(s). The method is useful to inhibit the adhesion of bacteria to such surfaces as teeth, other bacteria adhered to teeth, human oral epithelial cells, and human epithelial urinary tract cells, and to clean dental implants, bacterial fermentation vats, and the like.

BEST MODE OF THE INVENTION

Figure 1:
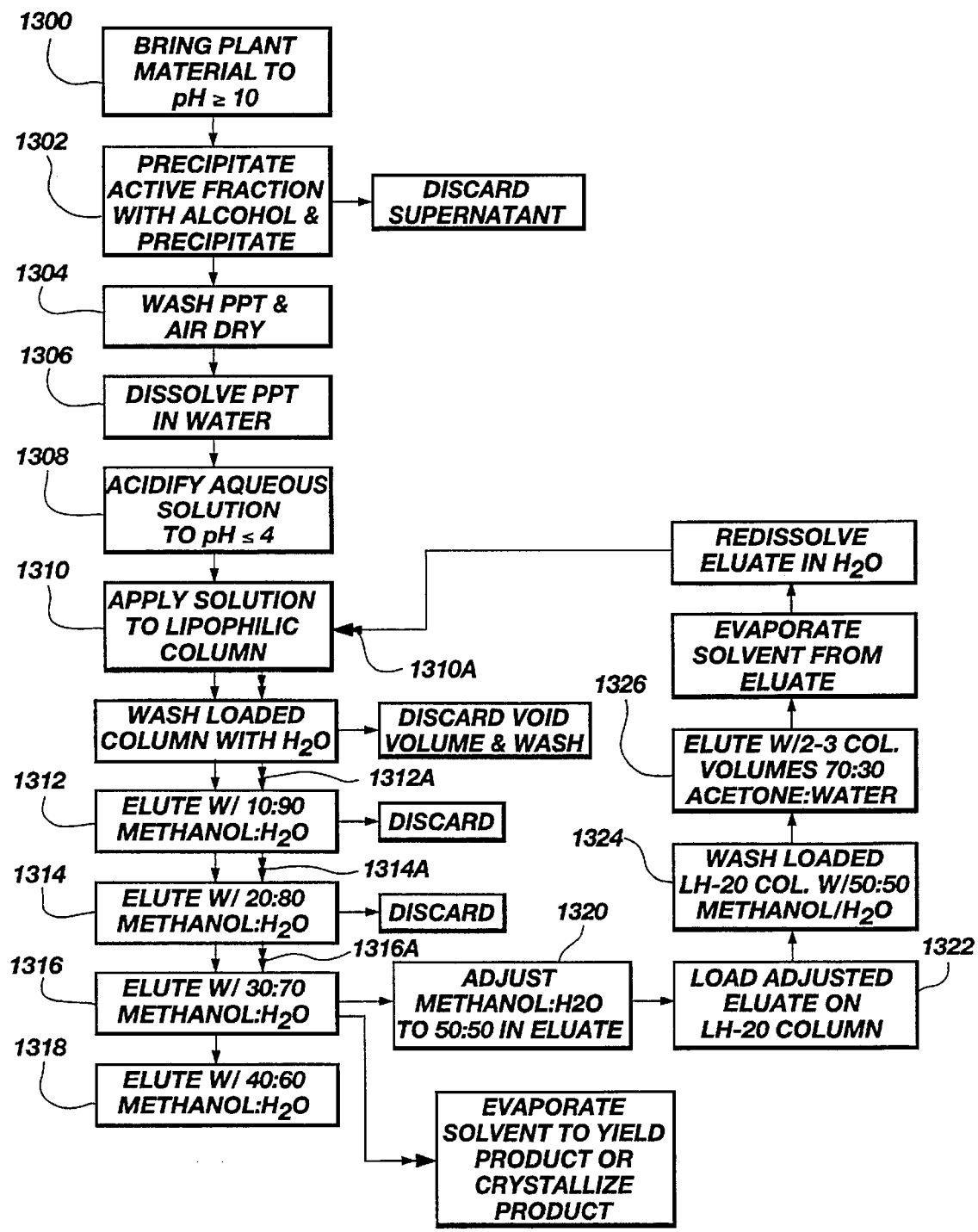
FIG. 1 is a flow chart of a method of preparing the compounds.

A. Processes:

As previously mentioned, the compositions useful for practicing the invention may be derived from a plant material extract. A method of preparing a plant extract having an active fraction which is active to inhibit adherence of non-viral microbes to cell surfaces, includes providing a homogenate of a plant material of a plant having a native active fraction comprising polyphenolic compounds having anti-adherence activity, adding a sufficient amount of a base to the homogenate to alkalinize the homogenate to a pH of greater than about pH 10 and to cause phenol groups of polyphenolic compounds to be ionized to phenoxide ions, and adding to the alkalinized homogenate, a sufficient amount of an alcohol to produce a precipitate of the polyphenolic compounds having phenoxide ions, and separating the precipitate. The method can also include fractionating the precipitate on a lipophilic column by step-wise elution with solutions containing varying ratios of an alcohol or other relatively non-polar water miscible organic solvent to water, beginning with a low alcohol:water ratio, to produce a series of step-wise eluates eluted at different alcohol:water ratios, and separating and identifying one of the eluates as substantially comprising the fraction having anti-adherence activity.

The method can further include fractionating the anti-adherence eluate on a column to separate substantially colorless polyphenolic compounds from colored anthocyanic compounds, fractionating the colorless polyphenolic compounds recovered from the column on a second lipophilic column by step-wise elution with solutions containing varying ratios of alcohol to water, beginning with a low organic solvent:water ratio, to produce a second series of step-wise eluates eluted at different organic solvent:water ratios, and separating and identifying one of the second series of eluates as having anti-adherence activity.

The presently preferred process for making the compounds involves first making a plant (e.g. cranberry) extract, and then substantially purifying an active compound from the extract. The preferred process is diagrammatically depicted in FIG. 1, and constitutes the hereinafter described EXAMPLE I. The process generally involves making an alkaline pH adjustment of an an aqueous solution of previously extracted plant material in which the "active" compounds are soluble.

B. Preferred Compounds:

Proanthocyanidin oligomers or polymers, useful for the present anti-microbial methods are comprised of monomeric flavanoids which include catechins, epicatechins, gallocatechins, galloepicatechins, flavanols, flavonols, and flavan-3,4-diols leucocyanidins and anthocyanidins. The proanthocyanidin polymers have 2 to 16 flavonoid units, preferably 2 to 15 flavonoid units, and most preferably 2 to 11 flavonoid units.

Additionally, the crystalline compound is found to have a melting point (M.P.) of greater than 280° C., and is observed to be extremely stable to oxidation during storage in atmosphere, leucocyanidins are known to have such a property.

In addition, it was found that crystal formation (1316A) occurred upon storage of the LH-20 70/30 eluate under nitrogen for periods of from one to several weeks or more (FIG. 1). Apparently, under slow purging of the nitrogen atmosphere, the eluate (generally 1–2 ml volume) becomes sufficiently concentrated that the purified active compound spontaneously crystallizes, such behavior is known for various polyphenolic compounds. Needle-like crystals are obtained from water, alcohol (e.g. MeOH or EtOH) or mixtures thereof.

Certain other compounds present in the cranberry extract have been further identified as having anti-adhesion activity, and in some cases are partially purified. These include leucocyanidins/leucodelphinidins and flavonol pyranosides. Catechin is described in the Merck Index #1908, epicatechin differs from catechin in the orientation of the hydroxyl at position 3. Procyanidins, also referred to as proanthocyanidins, are polymeric compounds composed of catechin and epicate, chin residues, formulae I through III depict dimers of epicatechin and catechin, with the epicatechin linked via C4 to the C8' of the catechin moiety A repeating unit of a polymeric procyanidin, catechin and epicatechin residues may be combined in all possible combinations in polymeric procyanidins up to molecular weights of up to about 5000 Daltons. Proanthocyanidin polymers are known to have a varying number of flavonoid units. The polymers preferably contain two to fifteen monomeric flavonoid subunits, most preferably two to eleven subunits. Leucocyanidin is described as Merck Index #5334, a closely-related compound is leucedelphinin. Myricetin-3-pyranoside, a compound identified and described as isolated from the present extract and found to have activity, myricetin is Merck Index #6244.

The anti-adhesion activity of the putative procyanidin and procyanidin polymers is believed to be potentiated or otherwise enhanced when combined with a substance selected from the group comprising flavanols, especially galloyl-substituted polyphenols including gallocatechin, gallo-epicatechin, and pyranosides or sulfates of these, leucocyanins, and flavonol pyranosides.

Of the flavonol pyranosides present in the Vaccinium extract, myricetin-3-pyranoside exhibits the highest anti-adherence in a metabolically unactivated form. In its native state, this compound has anti-adhesion activity, but less than that of the procyanidin(s).

Preferably, compounds having a ring system as shown in formula (IV), wherein the ring C includes oxygen at position 1 and having a pyranoside as $R^2$ has anti-adhesion activity. Leucoanthocyanins (exemplified as leucocyanin and leucodelphinin) are colorless compounds having the catechin or epicatechin ring structure with an saturated ring C and a pyranoside in the $R^2$ position. Upon treatment of leucocyanins by heating in aqueous acid solution, the O—$R^2$ carbohydrate linkage is hydrolyzed oxidized and ring C is oxidized, resulting in an unsaturated cyanidin (or delphinidin), wherein ring C is unsaturated and gives a characteristic red color. The material in certain HPLC peaks of the Vaccinium extract, which absorb at 280 nm and are found to contain anti-adhesion activity, are initially colorless. Upon treatment with heat and aqueous acid, carbohydrate moieties are released, ring C is oxidized, and red color appears in the fraction at the characteristic anthocyanin absorbance wavelength of 512 nm, and the activity in the material is lost. The oxidation state of ring C appears to play an important role in the mechanism of anti-adherence activity.

Further, quercetin and myricetin, which both share a slightly more oxidized catechin or epicatechin-like nucleus than the leucocyanins but have $R^2$=H, have been tested in the anti-adhesion assay and show no activity. However, myricetin-3-pyranoside isolated from Vaccinium species does have anti-adhesion activity.

Further as described previously herein, one of the anti-adhesion assays described herein compares the ability of a substance to inhibit binding relative to mannose inhibition of such adhesion, and it is therefore believed that a carbohydrate moiety is involved in conferring anti-adhesion activity, regardless of whether it is added prior to or as a result of metabolic activation.

It has been concluded that structures as shown in formula (IV), wherein Z=C, carbonyl, or O, $R^1$=H or OH, $R^2$=H, OH, pyranoside, a pyranoside chain, or galloyl; all possess some degree of inhibitory effect on adherence of microbes to cell surfaces. Further, the microbes whose adherence to cells is interfered with include bacteria and yeast which adhere to cell surfaces as a step in infecting them.

According to the literature (Hackett, et al., (1983) *Xenobiotica* 13(5), 279–86 and ibid., 12(7), 405–16) 90% of the disclosed polyphenol substances are metabolized into and excreted as catechin glucuronide and/or 3'-o-methyl-(+)-catechin glucuronide and/or 3'-o-methyl-(+)-catechin sulfate [82249-08-9], preserving the intact flavonol ring system.

C. Uses:

The presently preferred processes for using the compound involve inhibiting bacterial adhesion to surfaces (either therapeutically or prophylactically) comprising: providing the compound or other material (e.g. a Vaccinium extract enriched for anti-adherence activity and for 280 nm-absorbing and/or 360 nm-absorbing polyphenol compounds), and applying an effective mount of the compound in an acceptable carrier to a surface believed to have bacteria such as *E. coli* adhered thereto to disengage the bacteria from the surface. Desirably, the surface is rinsed to remove the disengaged bacteria. The method is useful to inhibit the adhesion of bacteria to such surfaces as teeth, other bacteria adhered to teeth, human oral epithelial cells, and human epithelial urinary tract cells; and to clean dental implants, bacterial fermentation vats, and the like.

D. Compositions:

The invention includes oral hygiene products containing the compound, as disclosed previously herein, having microbial anti-adhesion properties. Such oral hygiene products include, but are not limited to, dentifrices, oral rinses, and chewing gums.

A dentifrice of the invention would be made by preparing an effective amount of the "active ingredient" in a conventional powder or paste carrier, the carrier being comprised of ingredients including a hydrophilic base, emulsifiers, flavoring agents, fragrance agents, preservatives, etc., in conventional proportions. Such a dentifrice may include effective amounts of abrasive components for mechanical disruption/removal of tartar and/or fluoride. A specific example of a toothpaste includes ingredient in an amount of between about 0.2% and about 5% by dry weight in combination with toothpaste constituents.

A chewing gum would contain a conventional gum component, a preservative, and an effective amount of the active ingredient. In the gum, the amount of the active ingredient will generally be between about 0.5% and about 5% by dry weight.

An oral rinse may contain an aqueous or aqueous-alcohol liquid carrier, a preservative, and an effective amount of the active ingredient, the latter being generally between about 0.5% up to about 10% by volume, or 0.005 to 2% by dry weight.

Another product in which the extract and/or novel compounds find use is a throat spray or lozenge to treat a sore throat by, for example, reducing or preventing adhesion of deleterious bacteria to throat tissues.

At present it is believed preferable not to include strong oxidizing agents such as hydrogen peroxide, as these may cause unsaturation of the ring C in certain compounds thereby destroying their anti-adhesion activity.

It is also contemplated that the ingredient may be prepared in capsule or tablet form for regular administration to help maintain urinary tract health, and particularly as a prophylactic against urinary tract infections. Or, beverages enriched for the active ingredient could be prepared for a like purpose, making the known benefits of cranberry juice available to individuals who dislike the taste of cranberries. The active ingredient should be present in an amount of from 5 to 500 mg in a tablet form, or in an amount to provide a similar dosage in a 100 ml to 250 ml beverage.

The ingredient could also be prepared in compositions for treatment of urinary tract infections. In tablet form, such a composition would include from about 10 to about 500 mg of the ingredient per dose unit in a suitable inert carrier, with the dose to be taken 2–4 times daily. Optionally, one or more of the following may be included: phenazopyridine HCl for relief of acute symptoms (from about 50 mg to about 200 mg per dose unit); methenamine as an anti-infective agent (from about 50 mg to about 500 mg methenamine per dose unit); and a urinary acidifier such as sodium diphosphate, hippuric acid, ascorbic acid, or mandelic acid (from about 100 mg to about 500 mg per unit dose).

A foot powder according to the invention would typically include an effective concentration of the extract admixed with miconazole or clotrimazole, talc, starch, and possibly fragrance. When incorporated into an aerosol, a propellant would also be used.

A foot ointment or cream would typically include an effective amount of the extract, miconazole or clotrimazole, petroleum, lanolin, sodium lauryl sulfate, emulsifiers, and preservatives.

A foot solution would typically include the inventive extract, an antifungal such as miconazole or clotrimazole, and a solvent system (e.g., water and alcohol).

A vaginal cream for treating yeast infections would include the extract, an effective amount of an antifungal such as clotrimazole, miconazole or terconazole, benzyl alcohol, cetyl alcohol, and wax or other cream base.

EXAMPLES

Example I

As applied to an aqueous solution of OCEAN SPRAY cranberry powder ("OSCP solution"), the method went as follows. A sufficient amount of a strong base (e.g., NaOH) is added to the OSCP solution to bring it to a pH sufficient to ionize phenol groups of pelyphenols to phenoxide groups, (≧pH 10) (FIG. 1; step 1300). When the process was applied to the OSCP solution, the solution turned green upon reaching the necessary pH. For 1 liter of a saturated (20%) OSCP solution of cranberry powder, about 70–80 ml of 10N NaOH was used. The green, basic OSCP solution thus produced was then stirred with a sufficient amount of a simple alcohol to cause formation of a green precipitate (step 1302). About 4 volumes (4 liters) of MeOH were used. In place of MeOH, other 1 to 3 carbon alcohols miscible could have been used. The precipitate was allowed to settle, collected on filter paper, and then washed with a small volume (about ⅓ to ½ liter in the example) of "basic" MeOH (step 1304). "Basic" MeOH is MeOH alkalinized with about 1–2 ml of 10N NaOH per liter. The washed solids were air-dried, and the resulting light green powder, which contained increased levels of the active fraction as revealed by testing in a red blood cell ("RBC") agglutination assay, was stable for many months at room temperature. Most of the sugars were removed in this step. Generally, between about 70 and 80 grams of green powder were recovered per liter of 20% OSCP.

Next, a sufficient amount of the green powder was dissolved in 200 ml of water to make a strong or nearly-saturated solution (step 1306; generally 30–40 grams from the 20% OSCP solution (step 1302). The aqueous solution was then acidified to convert the phenoxide ions back to phenol groups, in the present case, by adding sufficient concentrated acid (e.g., about 13–16 ml of 12M HCl) to bring it to a pH between about 3 and 4 (step 1308). In the case of extraction from OSCP, the solution turned to a wine-red color upon reaching the appropriate pH. Undissolved solids were removed (e.g., by filtration or centrifugation), and the supernatant solution was applied to a C18 lipophilic column (Waters Cartridge) which had been preconditioned with MeOH and then washed with deionized water (step 1310). After the cranberry-derived solution had been loaded, the C18 column was washed with 2–3 column volumes of water and eluted in step-wise fashion with MeOH:$H_2O$ mixtures of varying proportion. For a 35 ml C18 column having about 200 ml of the acidified cranberry-derived solution loaded thereon, elution step 1312 was with 100 ml (2–3 column volumes) of a mixture of 10:90 MeOH/$H_2O$ (vol./vol.), elution step 1314 was with 100 ml of 20:80 MeOH/$H_2O$, elution step 1316 is 30:70 MeOH/$H_2O$, and elution step 1318 was with 40:60 MeOH/$H_2O$. Other water-miscible alcohols could have been substituted for MeOH, with appropriate adjustment to the alcohol:water proportions to achieve the desired separation. Also, other non-polar organic solvents in comparison to water (e.g., acetone or acetonitrile) could have been substituted for the alcohol. Further, other similar reverse-phase silica gel columns, such as C2 or C8 or phenyl or the like columns, may have been substituted for C18 or lipophilic Sephadox LH-20 or LH-60 or the like.

The eluate of step 1316 is highly enriched for anti-adhesion activity, and included the procyanidins and flavanoids. To further purify the procyanidin, the step 1316 eluant is brought to 50% MeOH (step 1320), either by evaporation and re-dissolution or by adding MeOH. This solution was then applied to a hydroxypropylated gel filtration column (e.g. LH-20 SEPHADEX column, available from Sigma Chemicals), which had been pre-conditioned with 50:50 MeOH/$H_2O$ (step 1322). The column volume should generally be about $1/10$ to about $1/2$ of the starting volume of the acidified solution. After loading the 50:50 MeOH-adjusted solution of the eluate on the LH-20 column, the column was washed with 50:50 MeOH/$H_2O$ (step 1324). The LH-20 column was then eluted with about 2–3 column volumes of 70% acetone in water (vol./vol.) (step 1326): the eluate evaporated to dryness and redissolved in water. The LH-20 column selectively separated catechins, procyanidin polymers, and perhaps other polyphenols absorbing at 280 nm from other polyphenolic compounds. To achieve a similar separation, a phenyl-SEPHAROSE column or an LH-60 column (Sigma Chemical Co. of St. Louis, Mo.) could have been substituted for the LH-20. Both LH-20 and LH-60 SEPHADEX comprise hydroxypropyl groups pendant via ether linkages from SEPHADEX beads, and making the SEPHADEX material more lipophilic.

The LH-20 eluate redissolved in water (in neutral form, or preferably acidified as in step 1308) was then applied to another C18 lipophilic column similar to that used in step 1310, and subjected to the same step-wise elution protocol (steps 1310A, 1312A, 1314A, 1316A). The eluate from step 1316A (30% MeOH eluant) contains substantially a single compound absorbing at 280 nm, eluting at 18–19 minutes in the analytical HPLC procedure outlined in FIG. 5. Generally, between about 0.03 and about 0.10 grams of the purified compound are recovered from 1liter of the 20% OSCP, that is, a recovery of about 0.01% to about 0.05%. This recovery of a single active compound is at least 20-fold the recovery of mixed active compounds achieved by the methods described previously herein.

Example II

Figures 2, 3:
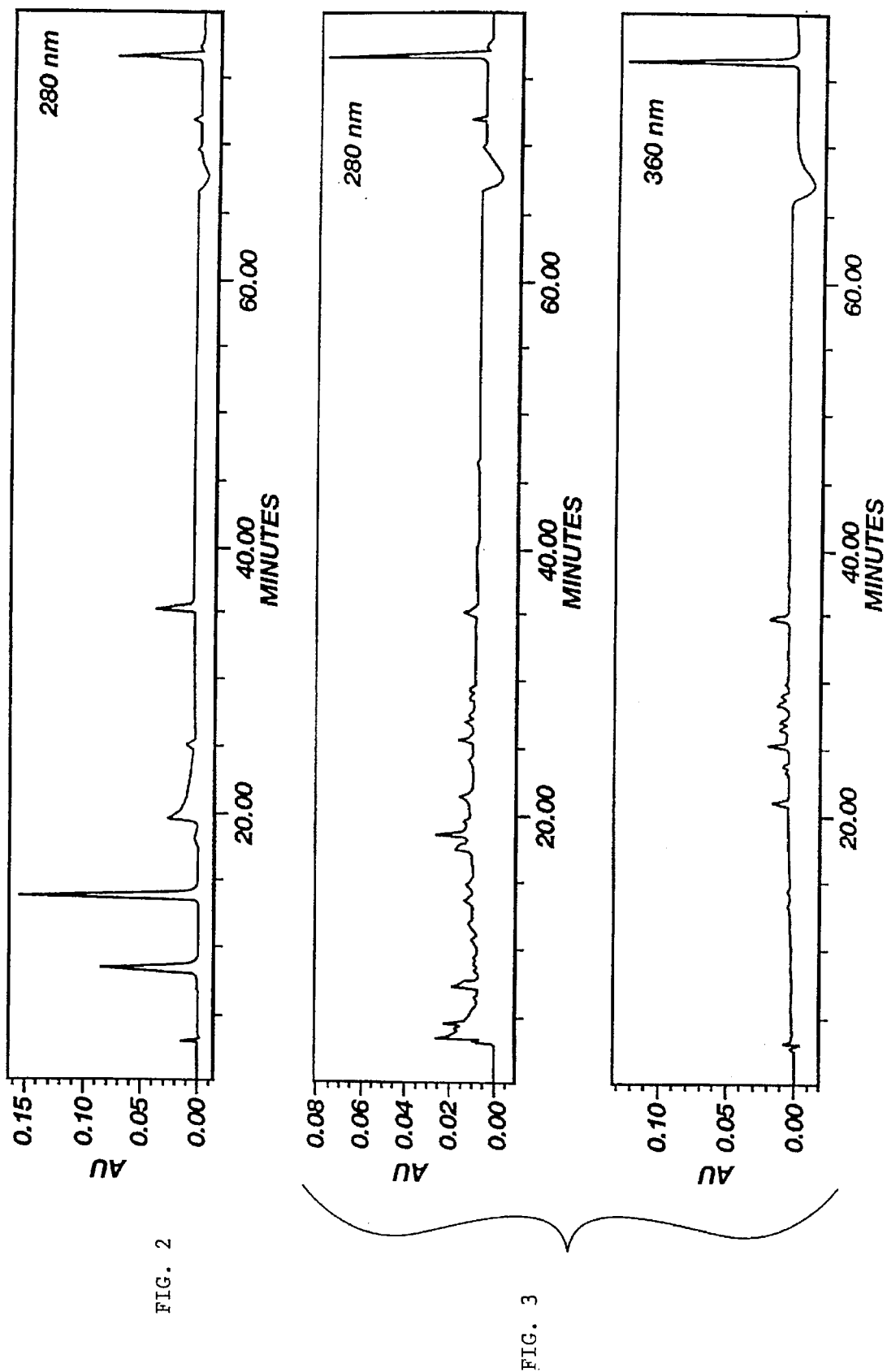
FIGS. 2–5 depict HPLC chromatograms of the products from selected steps of the process outlined in FIG. 1.
Figure 4:
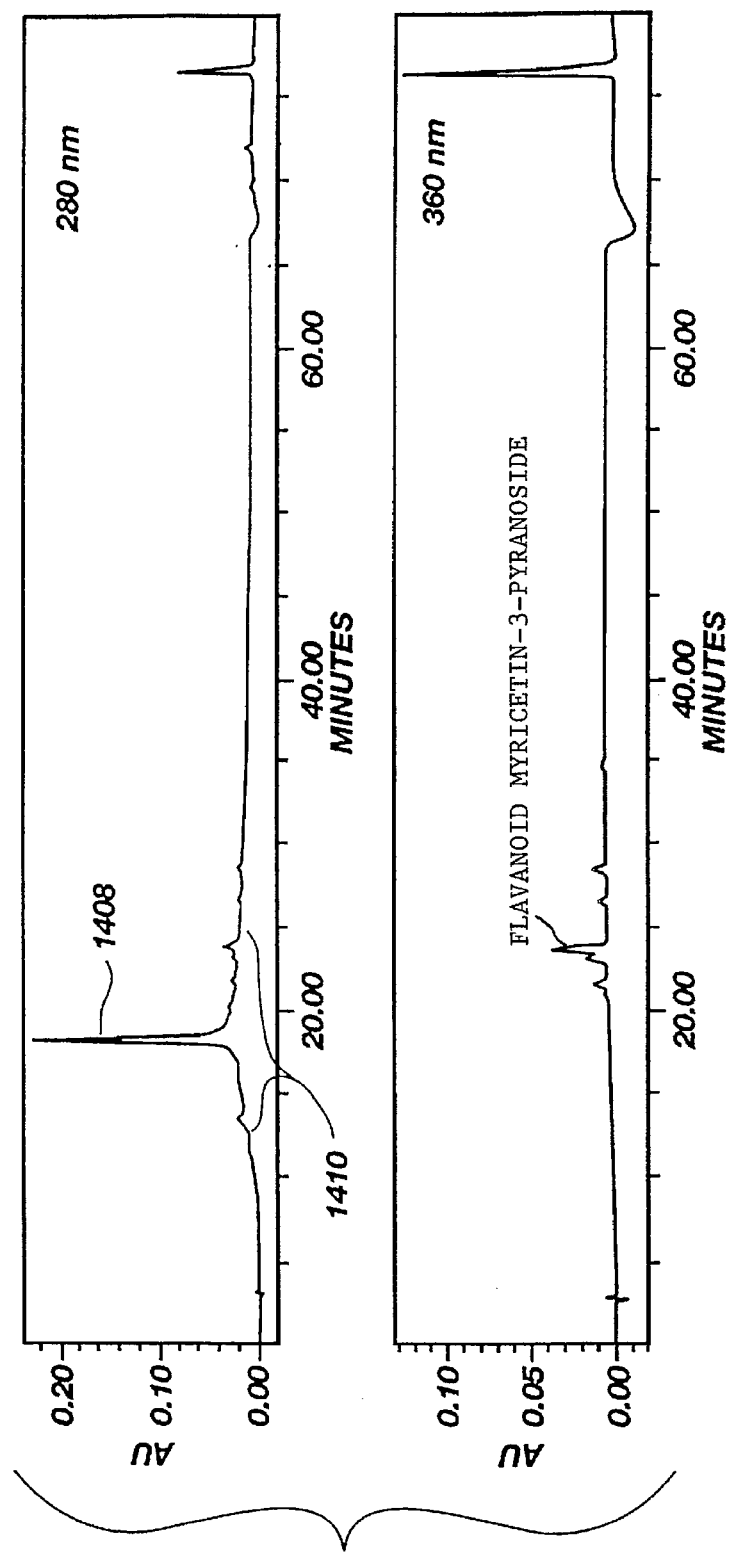
Figure 5:
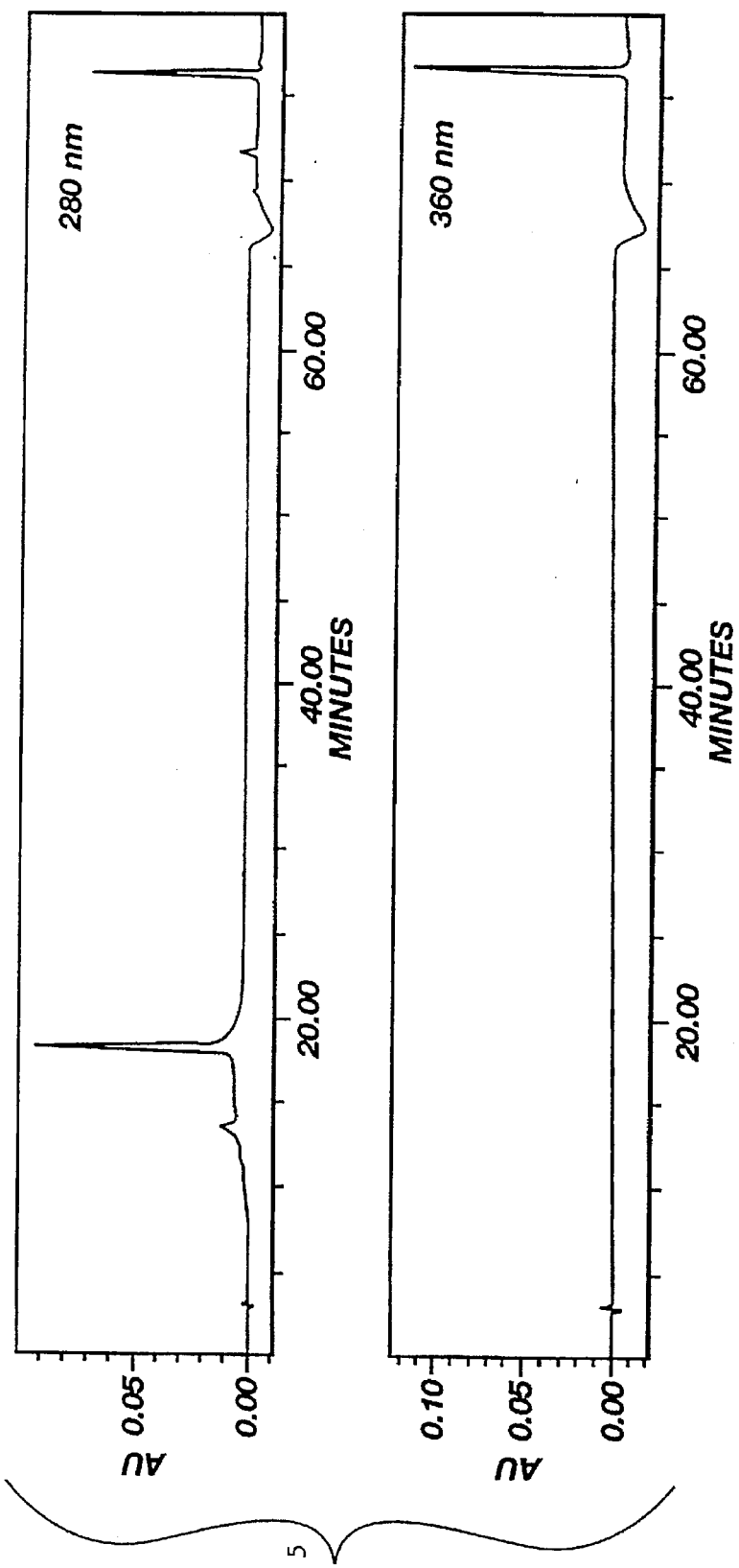

FIGS. 3–5 depict analytical HPLC chromatograms of products from various steps of the process of FIG. 1. FIG. 2 is an HPLC chromatogram showing the retention time of two marker standards, catechin (peak 1400) and epicate, chin (peak 1402), in the same HPLC protocol as FIGS. 3–5. FIG. 3 is a chromatogram of the product of the discarded supernatant, analyzed for compounds absorbing at 280 nm and for compounds absorbing at 360 nm. FIG. 4 shows a chromatogram of the product of step 1316, also analyzed for compounds absorbing at 280 nm and at 360 nm. FIG. 5 shows a chromatogram of the product of step 1316A, from which it is evident that essentially no 360 nm-absorbing compounds remain.

The eluate of step 1316A has been subjected to $^{13}C$ and $^1H$ nuclear magnetic resonance (NMR) analysis, mass spectrometry, and infrared absorbance analysis.

In FIGS. 2 to 5, a two-solvent linear gradient from 79% A/21% B (A=0.4% phosphoric acid, B=95% MeOH and 5% 0.4% phosphoric acid) to 35% A/65% B is run at a flow rate of 1 ml/min. over a time from 0 to 38.3 min. After 38.3 min., an isocratic flow at 35% A/65% B was maintained for an additional 21.7 min. The column is then washed with 100% MeOH for an additional 10 min. at a flow rate of 1.0 ml/min. Purified substances used for calibration are catechin (8.4 min.), epicatechin (14 min.), and quercetin (36 min.). One of the most active substances that occurs naturally in cranberry elutes at 19 min.

Figure 6:
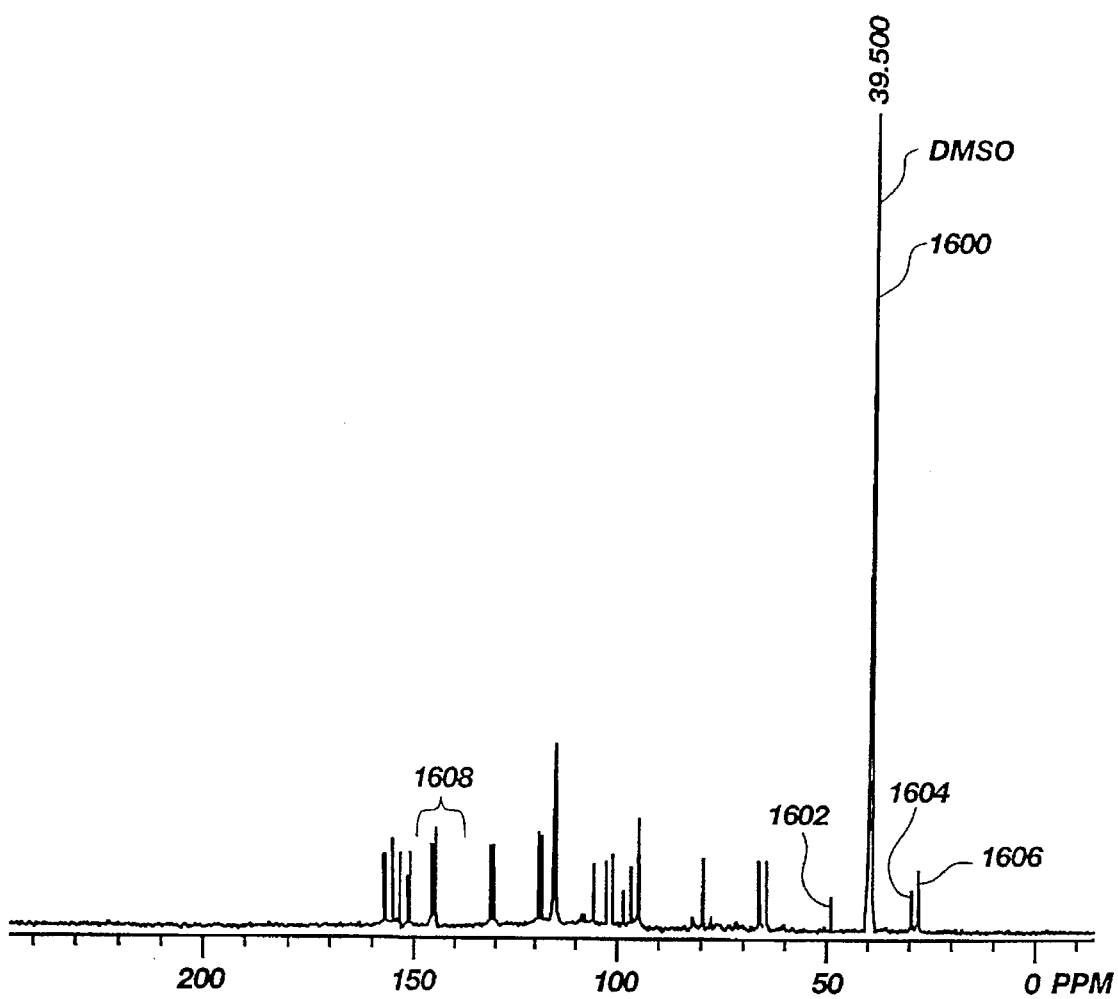
FIG. 6 is a chart depicting a $^{13}$C NMR spectrum of the isolated active material isolated as per FIG. 1.

FIG. 6 depicts a $^{13}C$-NMR scan of product from step 1316A, in $d_6$-dimethyl sulfoxide (DMSO). Peaks 1600 and 1602 are from the DMSO and MeOH solvents, respectively. Peak 1604 represents a C4 carbon of an epicatechin ring system, while peak 1606 represents a C4 carbon of a catechin ring system. Peaks 1608 represent the C3 and C4 carbons of a B-ring of a flavanol (catechin) ring system. The following information may be useful in interpreting the NMR of FIG. 6:

| | |
|---|---|
| Pulse Width = | 12.00 μSEC |
| ACQ Time = | 819.20 MSEC |
| Recycle Time = | .99 SEC |
| No. of ACQS = | 18,020 |
| Decoupler: Standard-64 Modulation | |
| Frequency = | 4.000 PFM |
| Power = | 2900/3000 |

Figure 7:
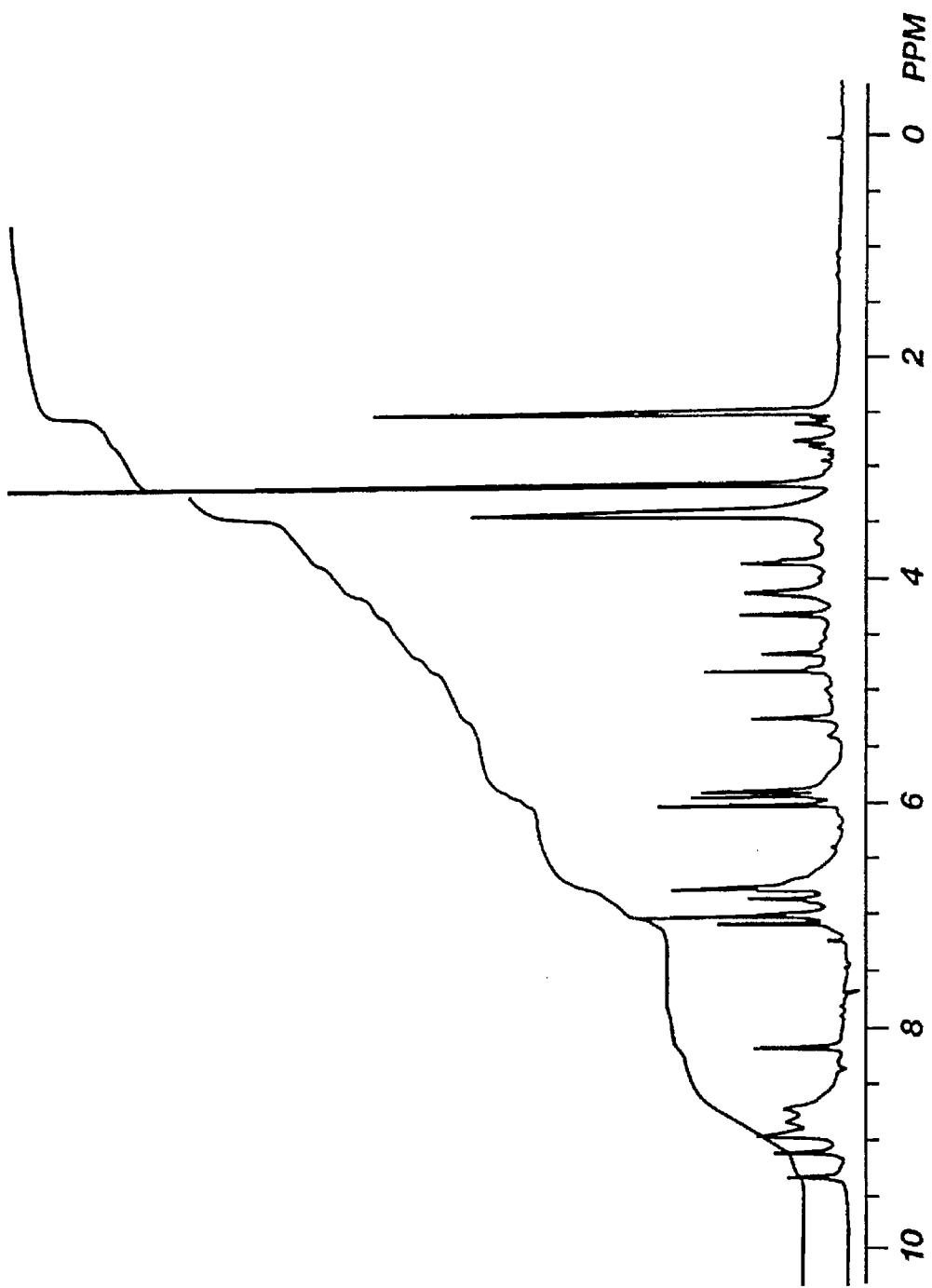
FIG. 7 is a chart depicting an $^1$H NMR spectrum of the isolated active material isolated as per FIG. 1.

FIG. 7 depicts an $^1H$-NMR scan of product from step 1316A, also in $d_6$-DMSO. The following information may be useful in interpreting the NMR of FIG. 7:

| One Pulse Sequence | |
| --- | --- |
| Pulse Width = | 3.00 μSEC |
| ACQ Time = | 1.36 SEC |
| Recycle Time = | 3.74 SEC |
| No. of ACQS = | 64 |

Figure 8:
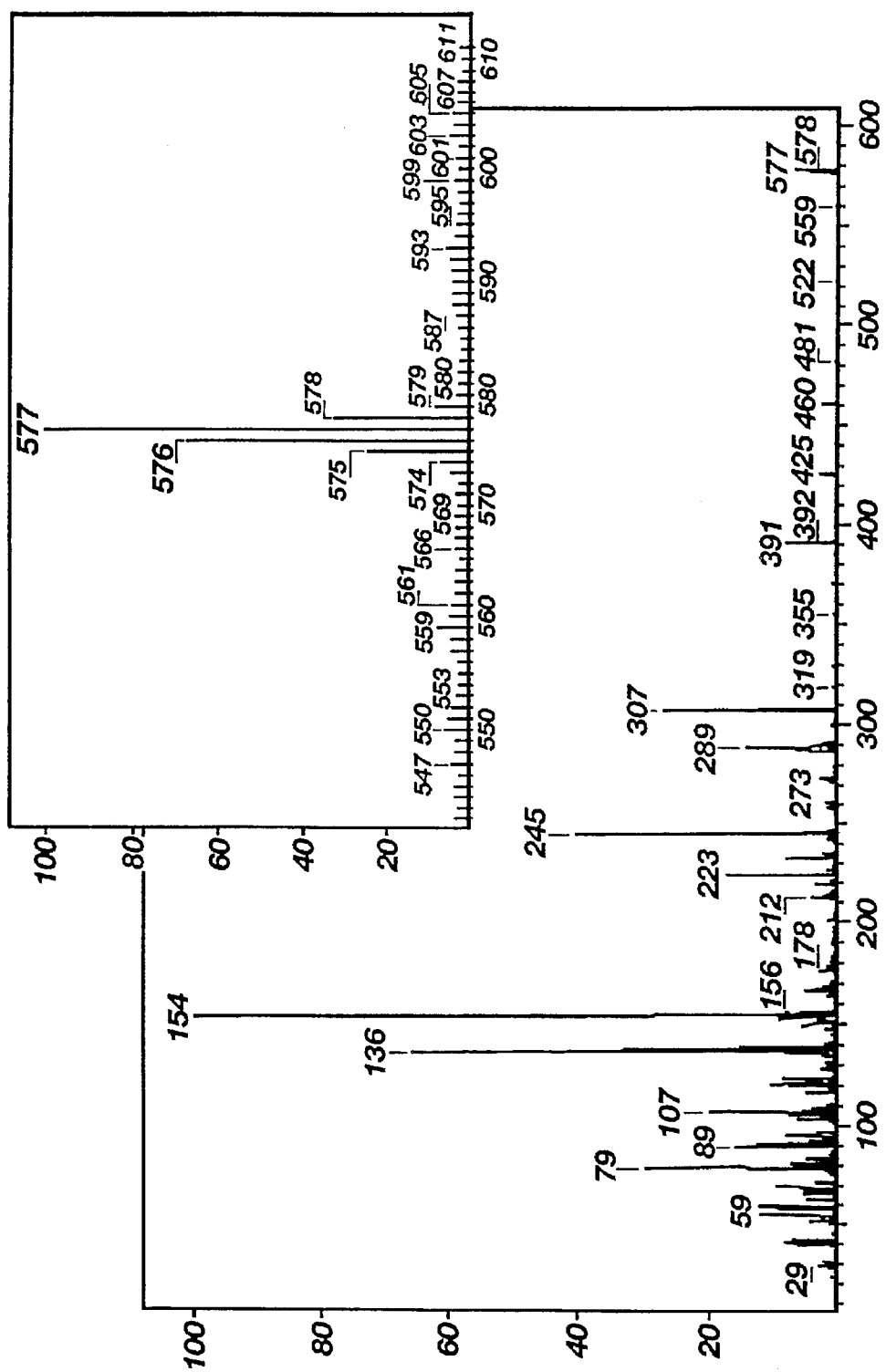
FIG. 8 is a chart of a mass spectrogram of isolated active material isolated as per FIG. 1.

FIG. 8 depicts a mass spectrogram of product from step 1316A, dissolved in 3-nitrobenzyl alcohol with DMSO.

Example III 500 mg of the compounds obtained from EXAMPLE II is added to 3.0 g of an already existing cranberry extract.

Example IV

The following test is used to test the ability of the compounds purified in the previous examples to inhibit agglutination of guinea pig red blood cells ("RBC") by *E. coli*.

Anti-adherence activity measured as interference with bacterial adherence to bladder cells: Human bladder epithelial cells are collected by centrifugation from the urine of a healthy female volunteer. The cells are washed in standard saline citrate (SSC) and resuspended to the desired volume. The optical density of the cell solution and cell counts are determined. *E. coli* bacterial strains isolated from urinary tract infections are cultured in tryptic soy broth at 37° C. for 72 hours to encourage piliation. The bacteria are also harvested by centrifugation, resuspended in the desired volume of SSC, and the approximate cell number determined.

A test tube is prepared containing 0.667 ml of a selected dilution of the substance to be tested for anti-adherence activity, plus 0.334 ml of the bacterial suspension. The bacteria are incubated with the test substance (isolated as per FIG. 1) for 15 min. at 37° C. Next, 1.0 ml of the bladder cell suspension is added to each tube and the tubes are incubated for a further 15 min. The compound is used in a 10 mg/ml solution.

After incubation, the content of each tube is filter through an 8 micron polycarbonate falter, and the falter is rinsed with two volumes (2 ml=one volume) of SSC to wash free any bacteria that are not adhered to the bladder cells. The filter is placed face down on a microscope and the cells are heat-fixed to the slide. The filter is removed, the slides are stained to visualize the cells, and the number of bacteria adhering per cell is counted for each of 20 cells per slide.

Two control tests are also performed. First, the bladder cells are incubated only in SSC without any bacterial suspension or test substance to determine how many bacteria originating in the urine sample are attached to the epithelial cells. Second, SSC is substituted for the test substance to determine the maximum number of bacteria that adhered to the cells without any inhibitor.

RBC, from guinea pigs as a suspension in Alsevers solution, is washed in SSC and resuspended in SSC. Human RBC, obtained by standard methods from the blood of volunteers, is prepared by washing and resuspending in SSC. Human RBC are believed to have a receptor for mannose-resistant pili of *E. coli*.

Cultured and prepared *E. coli* are tested as follows. A series of dots containing graded mounts of the test substance diluted in SSC, plus one dot containing SSC only, are placed on a polystyrene plate. The dots have a volume of about 10 μl. An equal volume of bacterial suspension is mixed into each dot, followed by ½ volume of RBC. The total volume in each dot, for a starting volume of 10 μl per dot, is thus 25 μl. The contents of each dot are thoroughly mixed and the degree of agglutination is scored on a scale of 0–4, with 0 representing no agglutination. The sum of the dot scores for all dilutions is totalled and subtracted from 32 to provide an Activity Index of activity interfering with agglutination.

The anti-adherence activity is compared.

The strain of *E. coli* used for the tests on adherence to human bladder cells is isolated from an active bladder infection in a human subject. This strain, designated the #3B strain, appears to possess both type 1 and P-type pili.

From the results, it is apparent that the compounds inhibit both type 1 pili-mediated adhesion of *E. coli* to guinea pig RBC and adhesion mediated by P-type pili.

The invention has been described with reference to specific embodiments, plant species and parts, and chemical procedures and the like; However, it will be recognized by those skilled in the art that various chemical substitutions can be made without departing from the spirit and scope of the invention. In particular, it is known that polyphenols, including flavonoids and anthocyanins, can be isolated and/or partially purified from plant materials by a number of different methods.

What is claimed is:

1. A method of interfering with non-viral microbial tissue adhesion to a body tissue comprising administering a therapeutically effective amount of a compound having a structure selected from the group of structures consisting of formulae I, II, and III:

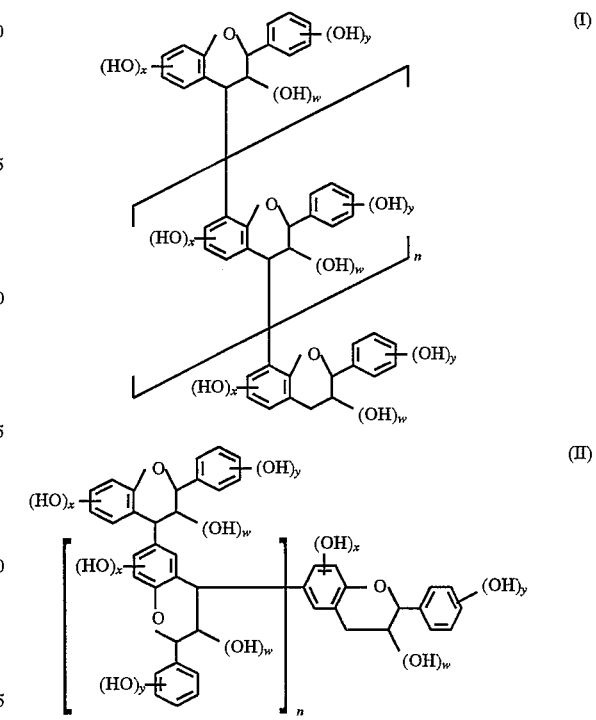

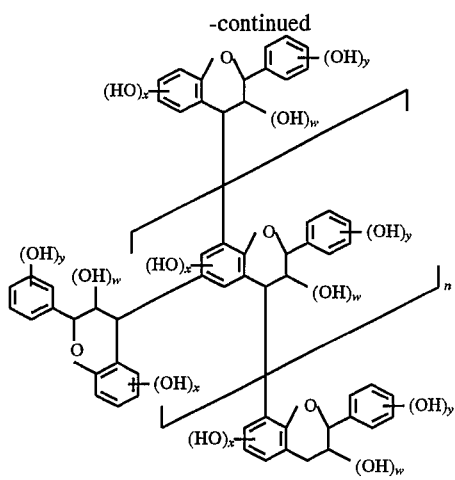

where X, Y=1 to 3, W=0 or 1, n=0 to 16.

2. The method of claim 1 wherein n=0 to 13.
3. The method of claim 1 wherein n=0 to 9.
4. A method of interfering with non-viral microbial tissue adhesion to a body tissue comprising administering a therapeutically effective amount of a compound consisting of two to eighteen monomeric flavanoid units having formula IV

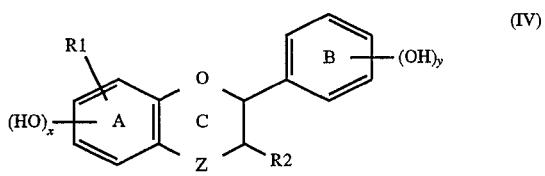

wherein x=0 to 2; y=0 to 3; Z=$CH_2$, carbonyl, $CHSO_3H$, galloyl, catechin, or epicatechin; $R^1$=H, pyranoside, galloyl, catechin, or epicatechin; and $R^2$=H, pyranoside, galloyl, or hydroxy.

5. The method of claim 4 in which the compound comprises 2 to 15 monomeric flavanoid units.
6. The method of claim 4 in which the compound comprises 2 to 11 monomeric flavanoid units.
7. A method of interfering with non-viral microbial tissue adhesion to a body tissue comprising administering a therapeutically effective amount of a compound consisting of two to eighteen monomeric flavanoid units having formula V

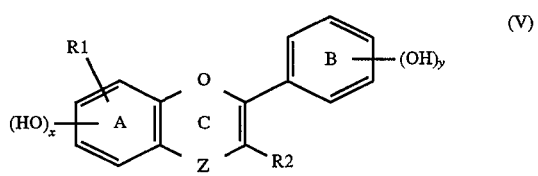

wherein x=0 to 2; y=0 to 3; Z=$CH_2$, carbonyl, $CHSO_3H$, galloyl, catechin, or epicatechin; $R^1$=H, pyranoside, galloyl, catechin, or epicatechin; and $R^2$=H, pyranoside, galloyl, or hydroxy.

8. A method of interfering with bacterial adhesion to a body tissue comprising administering a composition comprising a compound having a structure selected from the group of structures consisting of formulae I, II, and III:

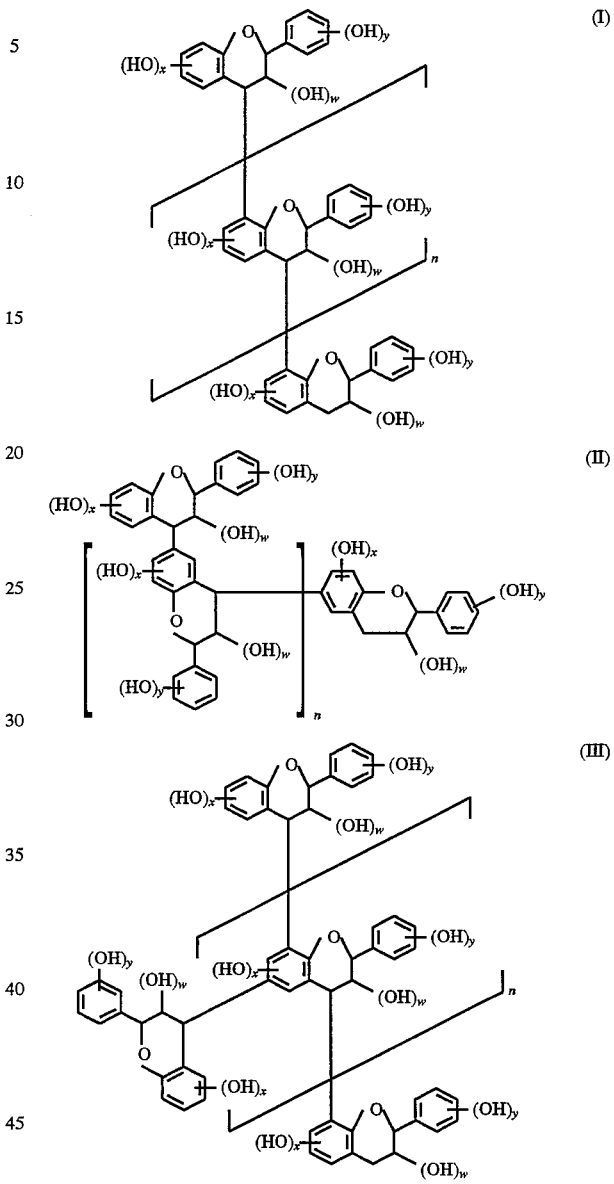

wherein X, Y=1 to 3, W=0 or 1, and n=0 to 16 and, to said body tissue in an amount effective to interfere with bacterial adhesion to the body tissue.

9. The method of claim 8, wherein said body tissue is selected from the group consisting of: gums, tooth surfaces, oral cavity mucosal tissues, throat mucosal tissues, genital mucosal tissues, and cervical surface tissues.

10. A method of using a compound having a structure selected from the group of structures consisting of formulae I, II, and III:

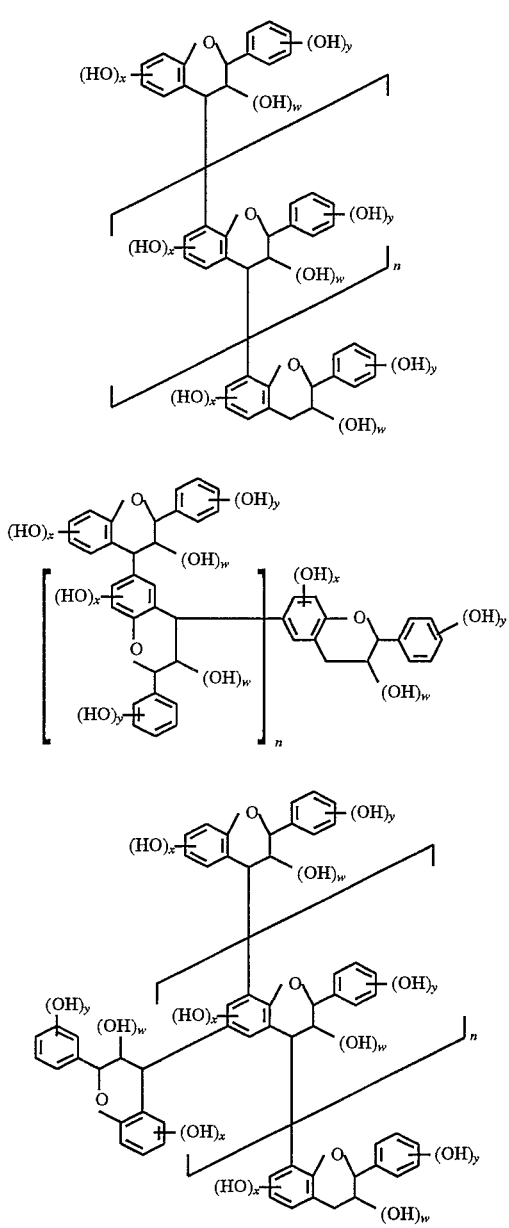

wherein X, Y=1 to 3, W=0 or 1, n=0 to 16, comprising oral administering said compound in a dosage sufficient to interfere with bacterial adherence to urinary tract tissues.

11. An extract of plant material enriched with a compound having a structure selected from the group of structures consisting of formulae I, II, and III:

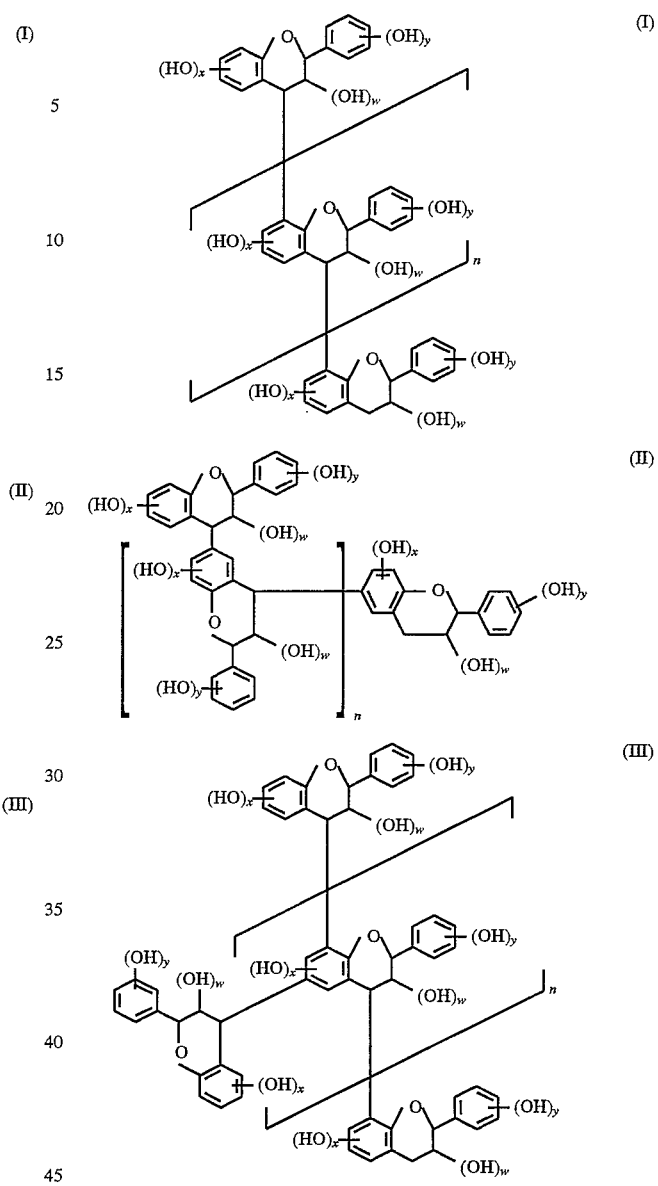

wherein X, Y=1 to 3, W=0 or 1, and n=0 to 16 and, wherein said compound is present in a proportion by dry weight of said extract which significantly exceeds a dry weight proportion of said compound in said plant material.

12. The extract of claim 11, wherein said plant material is from a plant of the genus Vaccinium.

13. The extract of claim 11, which further includes a second compound comprising a structure according to claim 1, wherein $R^2$=galloyl.

14. A composition of matter comprising:
   a compound having a structure selected from the group of structures consisting of formulae I, II, and III:

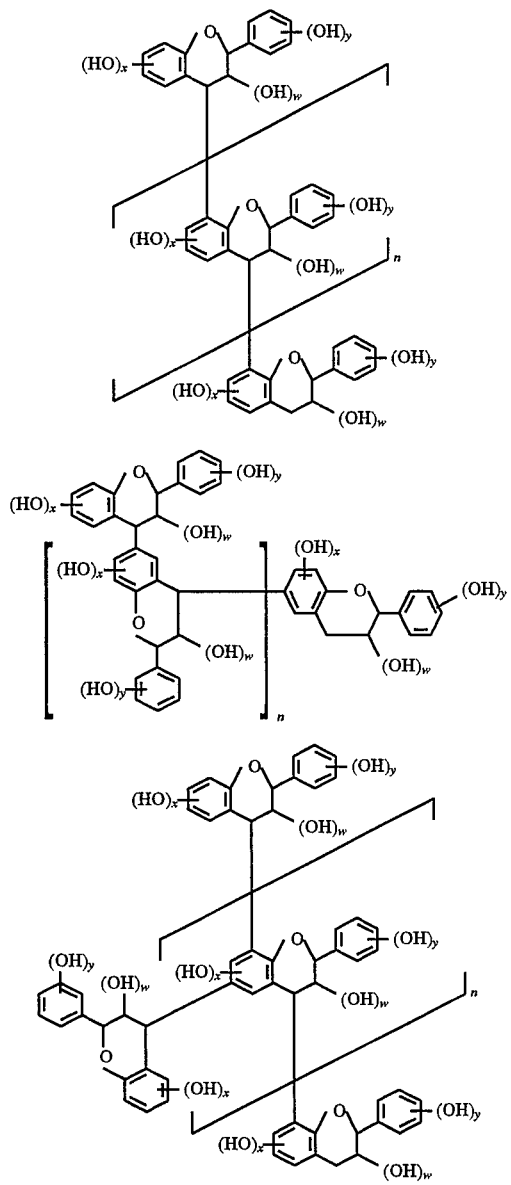
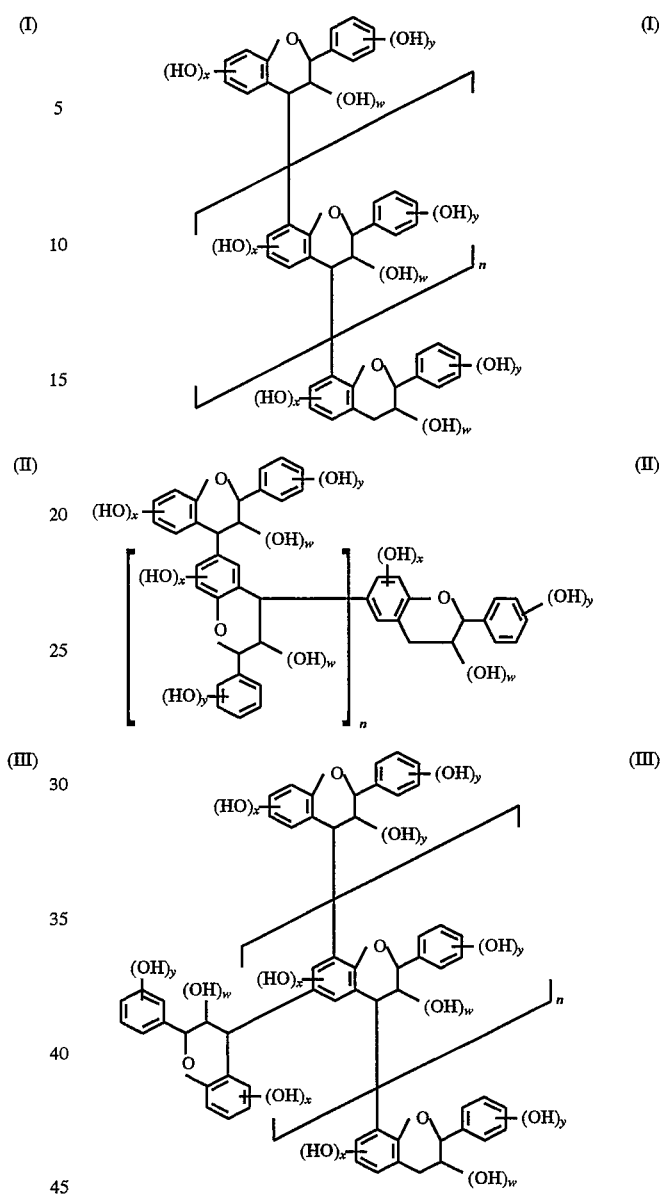

wherein X, Y=1 to 3, W=0 or 1, n=0 to 16; and one or more additional compounds selected from the group consisting of polyphenols in an amount effective to enhance anti-adhesion activity of said first compound.

15. The composition of claim 14, wherein said first compound is derived from plant material of a Vaccinium plant species.

16. The composition of claim 14, wherein said polyphenols include galloyl-substituted tannins and galloyl-substituted condensed polyphenols.

17. A composition comprising:

a compound having a structure selected from the group of structures consisting of formulae I, II, and III:

wherein X, Y=1 to 3, W=0 or 1, n=0 to 16, in an amount therapeutically effective to interfere with bacterial adhesion to a biological surface; and a pharmaceutically acceptable carrier.

18. The composition of claim 17, wherein the pharmaceutically acceptable carrier is selected from the group consisting of dental paste, powder, gel base compositions, aqueous solutions, aqueous-alcohol solutions suitable for oral rinsing or gargling, dental floss, artificial saliva and chewing gum.

19. The composition of claim 17, wherein said pharmaceutically acceptable carrier comprises a tablet or capsule and wherein said composition is present in an amount of between about 0.5 milligram and about 500 milligrams.

20. The composition of claim 17, wherein said pharmaceutically acceptable carrier is compatible with genital and cervical mucosal tissues and is selected from the group consisting of douches, suppository formulations, creams and jellies.

21. Crystalline proanthocyanadin having a melting point greater than 280° centigrade.

* * * * *

UNITED STATES PATENT AND TRADEMARK OFFICE
CERTIFICATE OF CORRECTION

PATENT NO. : 5,650,432
DATED : July 22, 1997
INVENTOR(S) : Walker et al.

It is certified that error appears in the above-indentified patent and that said Letters Patent is hereby corrected as shown below:

Column 3, line 54, change "glucumnide" to --glucuronide--;

Column 5, line 49, delete "an" first occurrence;

Column 6, line 17, change "epicate, chin residues" to --epicatechin residues--;

Column 6, line 28, change "leucedelphinin" to --leucodelphinin--;

Column 7, line 20, change "polyphenol" to --polyphenolic--;

Column 7, line 30, change "mount" to --amount--;

Column 8, line 53, change "pelyphenols" to --polyphenols--;

Column 8, line 66, change "10N" to --10 N--;

Column 9, line 14, change "12M" to --12 M--;

Column 10, line 8, change "1liter" to --1 liter--;

Column 10, lines 20 & 21, change "epicate, chin" to --epicatechin--;

Column 11, line 42, change "filter" to --filtered--;

Column 11, line 43, change "falter" to --filter-- both occurrences therefore;

Column 11, line 65, change "mounts" to --amounts--.

Signed and Sealed this

Seventeenth Day of March, 1998

Attest:

BRUCE LEHMAN

Attesting Officer

Commissioner of Patents and Trademarks